(12) United States Patent
Dilmaghanian (10) Patent No.: US 8,096,838 B2
(45) Date of Patent: Jan. 17, 2012

(54) HEADER ASSEMBLY FOR IMPLANTABLE MEDICAL DEVICES

(75) Inventor: Farshid Dilmaghanian, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 93 days.

(21) Appl. No.: 12/717,732

(22) Filed: Mar. 4, 2010

(65) Prior Publication Data

US 2010/0233896 A1    Sep. 16, 2010

Related U.S. Application Data

(60) Provisional application No. 61/159,313, filed on Mar. 11, 2009.

(51) Int. Cl.
*H01R 24/04* (2006.01)
(52) U.S. Cl. ........................................ 439/669
(58) Field of Classification Search .................. 439/669, 439/668; 607/37
See application file for complete search history.

(56) References Cited

U.S. PATENT DOCUMENTS

| | | | |
|---|---|---|---|
| 4,072,154 A | 2/1978 | Anderson et al. | |
| 4,105,037 A | 8/1978 | Richter et al. | |
| 4,202,592 A | 5/1980 | Rullier et al. | |
| 4,262,673 A | 4/1981 | Kinney et al. | |
| 4,461,194 A | 7/1984 | Moore | |
| 4,934,366 A | 6/1990 | Truex et al. | |
| 5,070,605 A * | 12/1991 | Daglow et al. | 29/842 |
| 5,132,495 A * | 7/1992 | Ewing et al. | 174/138 F |
| 5,257,622 A * | 11/1993 | Hooper et al. | 607/37 |
| 5,413,595 A | 5/1995 | Stutz, Jr. | |
| 5,817,984 A | 10/1998 | Taylor et al. | |
| 5,866,851 A | 2/1999 | Taylor et al. | |
| 6,029,089 A | 2/2000 | Hawkins et al. | |
| 6,039,685 A | 3/2000 | Bushek | |
| 6,112,121 A | 8/2000 | Paul et al. | |
| 6,192,277 B1 | 2/2001 | Lim et al. | |
| 6,428,368 B1 | 8/2002 | Hawkins et al. | |
| 6,498,952 B2 | 12/2002 | Imani et al. | |
| 6,671,554 B2 | 12/2003 | Gibson et al. | |
| 6,736,770 B2 | 5/2004 | Leysieffer et al. | |
| 6,878,013 B1 | 4/2005 | Behan | |
| 6,879,857 B2 | 4/2005 | Swanson et al. | |
| 6,895,276 B2 | 5/2005 | Kast et al. | |
| 7,003,351 B2 | 2/2006 | Tvaska et al. | |

(Continued)

FOREIGN PATENT DOCUMENTS

WO    WO 2006/078548 A2    7/2006

(Continued)

OTHER PUBLICATIONS

Partial European Search Report mailed Jun. 4, 2010 from corresponding European Patent Application No. 10002416.5 (5 pages).

*Primary Examiner* — Neil Abrams (74) *Attorney, Agent, or Firm* — Klein, O'Neill & Singh, LLP (57) ABSTRACT

A header assembly for an implantable medical device (IMD). The header assembly includes a plurality of cavities with a plurality of insulating rings interdisposed between adjacent ones of the cavities. The cavities receive electrical contact rings. In certain embodiments, the insulating rings are formed integrally with a body of the header assembly.

18 Claims, 3 Drawing Sheets

U.S. PATENT DOCUMENTS

| | | |
|---|---|---|
| 7,047,077 B2 | 5/2006 | Hansen et al. |
| 7,062,329 B2 | 6/2006 | Ostroff |
| 7,063,563 B1 | 6/2006 | Hsu |
| 7,070,455 B2 | 7/2006 | Balsells |
| 7,083,474 B1 | 8/2006 | Fleck et al. |
| 7,108,549 B2 | 9/2006 | Lyu et al. |
| 7,155,283 B2 | 12/2006 | Ries et al. |
| 7,164,951 B2 | 1/2007 | Ries et al. |
| 7,167,749 B2 | 1/2007 | Biggs et al. |
| 7,187,974 B2 | 3/2007 | Haeg et al. |
| 7,195,523 B2 | 3/2007 | Naviaux |
| 7,210,968 B1 | 5/2007 | Gister et |
| 7,231,253 B2 | 6/2007 | Tidemand et al. |
| 7,241,180 B1 | 7/2007 | Rentas Torres |
| 7,263,401 B2 | 8/2007 | Scott et al. |
| 7,274,963 B2 | 9/2007 | Spadgenske |
| 7,299,095 B1 | 11/2007 | Barlow et al. |
| 7,303,422 B2 | 12/2007 | Hoffer et al. |
| 7,326,083 B2 | 2/2008 | Mehdizadeh et al. |
| 7,429,199 B2 | 9/2008 | Burgess |
| 7,515,964 B1 | 4/2009 | Alexander et al. |
| 7,610,089 B1 | 10/2009 | Rodriguez et al. |
| 7,717,754 B2 | 5/2010 | Ries et al. |
| 2003/0163171 A1 | 8/2003 | Kast et al. |
| 2004/0034393 A1 | 2/2004 | Hansen et al. |
| 2006/0224208 A1 | 10/2006 | Naviaux |
| 2008/0246231 A1 | 10/2008 | Sjostedt et al. |
| 2008/0255631 A1 | 10/2008 | Sjostedt et al. |
| 2009/0048638 A1 | 2/2009 | Rey et al. |

FOREIGN PATENT DOCUMENTS

| | | |
|---|---|---|
| WO | WO 2009/009299 A1 | 1/2009 |

* cited by examiner

HEADER ASSEMBLY FOR IMPLANTABLE MEDICAL DEVICES

CROSS-REFERENCE TO RELATED APPLICATION

This is a regular utility application of provisional application Ser. No. 61/159,313 filed Mar. 11, 2009, the contents of which are expressly incorporated herein by reference.

BACKGROUND

Aspects of the disclosed embodiments relate to an in-line connector for conducting electrical signals between two different sources or nodes and more particularly to implantable medical devices (IMDs), specifically to headers for IMDs.

RELATED ART

Some implantable medical devices provide electrical stimulation to body tissues, such as for monitoring or treating physiologic conditions and for providing alternative treatments to drugs. Exemplary implantable medical devices include implantable cardio defibrillators, pacemakers, and programmable neurostimulator pulse generators, which are collectively referred to herein as implantable medical devices or IMDs. The IMDs typically incorporate a hermetically sealed device enclosing a power source and electronic circuitry, known as a can, and a header assembly connected to the can.

Example IMDs are described in application Ser. No. 11/839,103, filed on Aug. 15, 2007, entitled Connector Assembly for Use with Medical Devices; application Ser. No. 12/062,895, filed on Apr. 4, 2008, entitled Connector Assembly for Use with Medical Devices; and application Ser. No. 12/100,646, filed on Apr. 10, 2008, entitled Integrated Header Connector System. The contents of each of these applications are expressly incorporated herein by reference.

Industry wide standards often exist for, among other things, the dimensions, size, pin spacing, diameter and the like for the header assembly and the medical lead cable. However, it is desirable to create a header assembly that includes reduced spacing between contact elements and thus, a reduced overall size of the header assembly. Furthermore, it is desirable to maintain good electrical contact during the life of the IMD, and to avoid disconnecting the medical lead cable from the receptacle located in the header. Yet the medical lead cable is desirably detachable for implanting and programming purposes and for replacing the IMD when necessary.

SUMMARY

The various embodiments of the present header for implantable medical devices have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description" one will understand how the features of the present embodiments provide advantages, which include reduced complexity of manufacture and assembly, with concomitant cost savings.

One aspect of the present header for implantable medical devices is to provide viable options for medical device manufacturers to reduce the overall dimensions of existing receptacles that otherwise may create manufacturing challenges. Among other things, placing stackable rings between electrically insulating seals and positioning conductive contact elements between conductive grooves for forming a receptacle and integrating the contact assembly into the IMD are difficult, costly, and time consuming. Accordingly, there is a need for a receptacle that not only meets the challenges associated with implantable applications but also is easier to manufacture than a variety of existing receptacles. There is also a need for a receptacle that is easily adaptable with existing implantable medical devices that are easier to manufacture than a variety of existing implantable medical devices. Further, it is desirable to reduce the size of the IMD and its header assembly.

One embodiment of the present header assembly for implantable medical devices comprises a body portion defining a plurality of openings spaced axially along the body portion; and a plurality of elastomeric walls interdisposed between adjacent openings to define cavities within the body portion, where each of the elastomeric walls defines an aperture passing axially through the body portion. The header also comprises a plurality of electrical contact rings each including an outer ring contact element and an electrical contact element housed in abutting engagement in an interior of the outer ring contact element. The electrical contact rings are configured to be positioned within the cavities such that adjacent elastomeric walls capture the electrical contact elements therebetween.

Another embodiment of the header assembly for an implantable medical device comprises a body portion defining a plurality of first openings spaced axially along the body portion; and a plurality of elastomeric walls interdisposed between the adjacent first openings to define first cavities within the body portion, where each elastomeric wall defines an aperture passing axially therethrough. The header assembly also comprises a first plurality of electrical contact rings positioned within the cavities between the elastomeric walls to form channels wherein the elastomeric walls form side walls of the channel and the electrical contact ring forms a base wall of the channel. The side walls are configured to capture a canted-coil spring housed within the electrical contact rings with no intervening portion of the electrical contact ring disposed between the canted-coil spring and the side walls.

Another embodiment is a method of assembling a header for an implantable medical device which comprises providing a unitary body portion defining a plurality of openings spaced axially along the body portion, and a plurality of elastomeric walls interdisposed between the adjacent openings to define cavities within the body portion, where each elastomeric wall defines an aperture passing axially therethrough; inserting an electrical contact ring comprising an outer ring contact element and an electrical contact element housed in abutting engagement in an interior of the outer ring contact element into each cavity; and capturing the electrical contact elements within the elastomeric walls of the cavities with no intervening portion of the electrical contact ring disposed between the electrical contact element and the elastomeric walls.

BRIEF DESCRIPTION OF THE DRAWINGS

The various embodiments of the present header for implantable medical devices now will be discussed in detail with an emphasis on highlighting the advantageous features. These embodiments depict the novel and non-obvious header shown in the accompanying drawings, which are for illustrative purposes only. These drawings include the following figures, in which like numerals indicate like parts.

DETAILED DESCRIPTION

The following detailed description describes the present embodiments with reference to the drawings. In the drawings, reference numbers label elements of the present embodiments. These reference numbers are reproduced below in connection with the discussion of the corresponding drawing features.

A header or header assembly for an IMD provides a means for electrically communicating, via an external medical lead cable, between the electronic circuits or power source located inside the device and the actual stimulation point. Generally, the header assembly includes a plurality of electrical contact elements, typically between three and seven, that are stacked in-line, or up to 14 or more in two rows. The contact elements are electrically coupled to the electronic circuits or to the power source located inside the can via conductive terminals. The contacts are separated electrically by dielectric insulator seals. The seals resist migration of body fluids into the spaces between the electrical contacts. Another desirable characteristic of the seals and possibly the contacts is adequate sealing force around the lead to maintain body fluid sealing to the lead while still providing acceptable insertion force. Other desirable characteristics of the IMD include reduced spacing between contact elements and reduced overall size of the header and IMD.

There are two generally accepted methods of manufacturing a header assembly for an IMD. In the first, a plurality of connectors with elastomeric seals is over-molded with a polymer to form the header assembly. In the second, contacts inclusive of a housing and a spring are inserted into cavities pre-molded into an elastomeric header. In both cases, the canted-coil springs of the contact elements have metal housing sidewalls to capture the springs. In the case of the over-molded header, there are separate seals and housing/spring contacts.

Certain of the present embodiments avoid metal sidewalls for the housing to retain the spring and reduce the number of seals, for example by using the over-molded header concept. In reducing or eliminating the sidewalls, these embodiments reduce the spacing between contacts and the overall size of the header and IMD. Accordingly, a feature of the present header is an in-line contact connector comprising a plurality of contact elements positioned in-line along a common bore and wherein the pitch, or spacing between two adjacent contact elements, is reduced compared to similar in-line contacts that have metal sidewalls.

By pre-molding an elastomeric header with individual cavities to accept contact elements, contact spacing can be reduced, as further discussed below. The elastomeric walls between contacts in the present embodiments achieve at least three advantages. First, the walls are dielectric insulators between contacts. Second, the walls serve as elastomeric seals between contacts. Third, the walls capture the canted-coil spring for each contact. These and other features and advantages of the present invention can be better understood in connection with the description, claims, and appended drawings.

Figure 1:
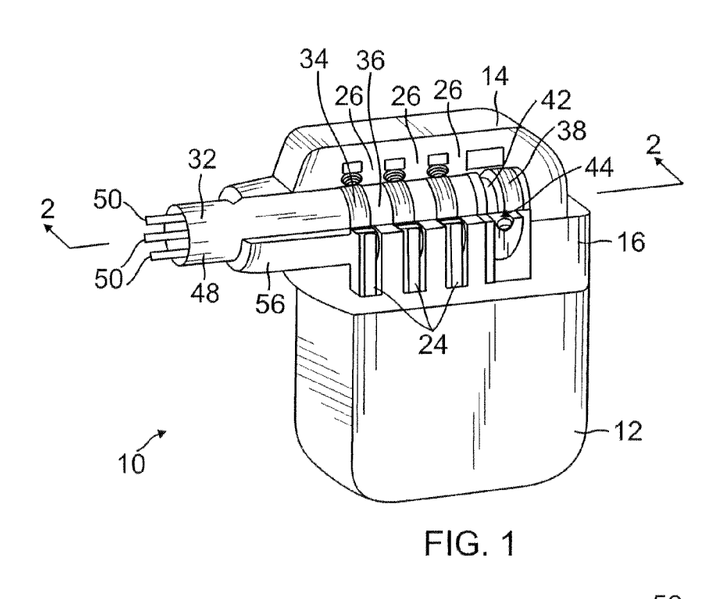
FIG. 1 is a front perspective view of an IMD including one embodiment of the present header, showing the header in partial section.
Figure 2:
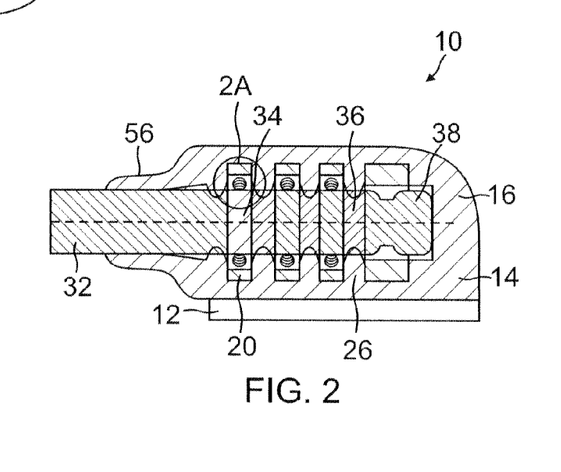
FIG. 2 is a front cross-sectional view of the IMD of FIG. 1, taken through the line 2-2 in FIG. 1.
Figure 4:
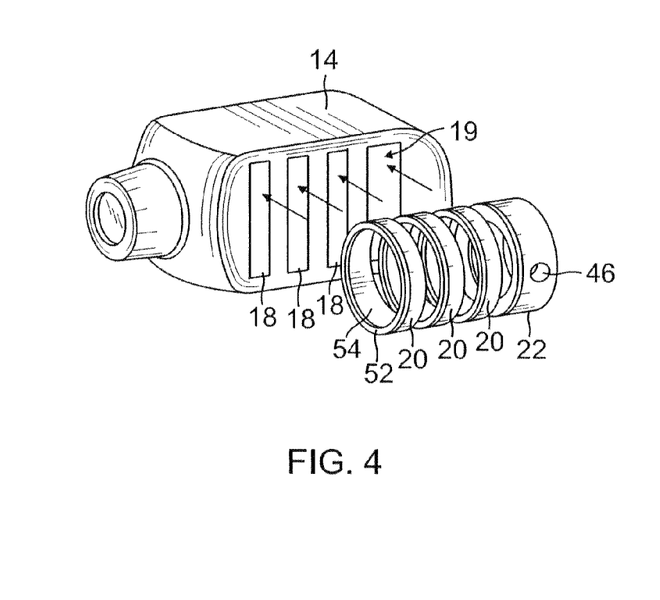
FIG. 4 is a front perspective view of the components of FIGS. 3-3B in a partially disassembled state.

With reference to FIGS. 1 and 2, one embodiment of the present implantable medical device 10 comprises a can 12. The can 12 houses a power source and electronic circuitry (not shown) and may be hermetically sealed to protect its contents. A header 14 including a body portion 16 adjoins the can 12. With reference now to FIG. 4, the header 14 includes a plurality of axially spaced openings 18 or slots, each of which may be appropriately sized and shaped to receive an electrical contact ring 20 or a holding ring 22. The contact rings 20 and the holding ring 22 are described in further detail below.

Figure 3:
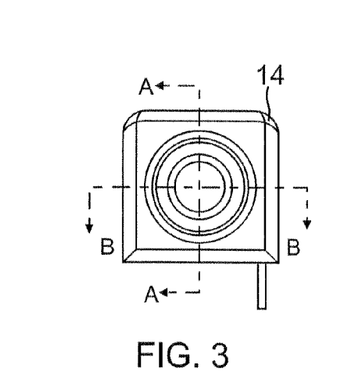
FIG. 3 is a left-side elevation view of the header of FIG. 1 including electrical contact rings and a holding ring.
Figure 3A:
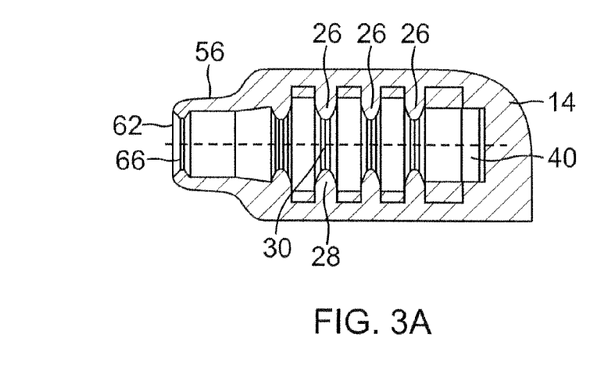
FIG. 3A is a front cross-sectional view of the components of FIG. 3, taken through the line A-A in FIG. 3.
Figure 3B:
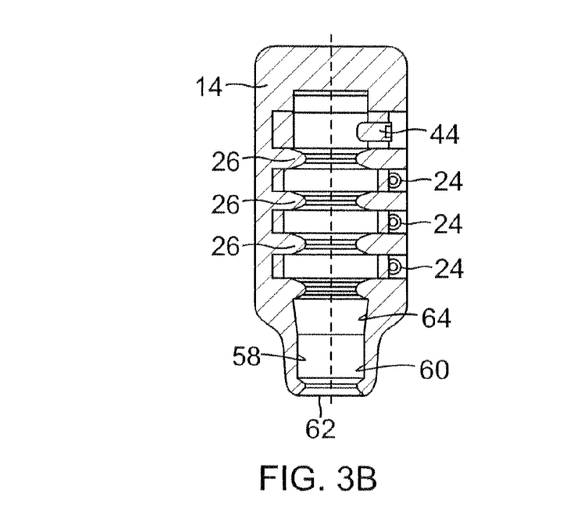
FIG. 3B is a top cross-sectional view of the components of FIG. 3, taken through the line B-B in FIG. 3.

With reference to FIGS. 1 and 3B, electrical leads 24 extend between the power source in the can 12 and the contact rings 20. The leads 24 may project through one or more feed-through terminals (not shown) passing through the sealed can 12 to reach the contact rings 20.

With reference to FIGS. 1 and 3A, insulating rings 26 are interdisposed between the openings 18 to create and define internal cavities or sections 19 within the body portion 16. The insulating rings 26 separate the cavities 19 into sections and electrically isolate each contact ring 20 from a neighboring contact ring 20. The insulating rings 26 also seal against the lead cable 32, as discussed in further detail below. Accordingly, these components are referred to alternatively herein as insulating rings 26 and sealing rings 26.

With reference to FIG. 3A, each insulating ring 26 substantially comprises a flat dividing wall 28 that defines a circular opening or aperture 30 at or near its center. The circular openings 30 are axially aligned along a common bore. As described in further detail below, in certain of the present embodiments the insulating rings 26 are molded integrally with the header body portion 16.

Figure 2A:
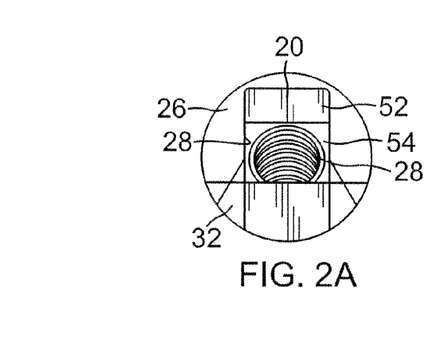
FIG. 2A is a detail view of the circled portion of the IMD of FIG. 2.

Thus, the header 14 comprises a body portion that defines a plurality of openings 18 spaced axially along the body portion 16. The plurality of insulating rings 26 interdisposed between adjacent openings 18 create and define the cavities or sections 19 within the body portion 16. The insulating rings 26 each define an aperture 30 that passes axially through the insulating rings. The electrical contact rings 20 are configured to be inserted into the openings 18 and positioned within the cavities 19 between the dividing walls 28 of the insulating rings 26. As shown in FIG. 2A, once the contact rings 20 are inserted between the dividing walls 28, a channel is formed that has the electrical contact ring 20 as a base wall of the channel and the dividing walls 28 on either side of the electrical contact ring 20 forming side walls of the channel. As described in greater detail below, the channel is configured to capture and retain an electrical contact element 54, but without the use or the need for metal or otherwise conductive housing side walls.

Together, the header 14, contact rings 20, insulating rings 26 and holding ring 22 may comprise a connector assembly configured to receive a lead cable 32, as shown in FIGS. 1 and 2, such as a medical lead cable comprising electrode leads. Further, although the illustrated connector assembly includes three contact rings 20 and three insulating rings 26, the present embodiments are not limited to any particular number of contact rings 20 or insulating rings 26.

With reference again to FIGS. 1 and 2, the lead cable 32 includes a plurality of ring-shaped electrical terminals 34 interposed between a plurality of ring-shaped lead insulators 36. When properly inserted within the header 14, the electrical terminals 34 engage the electrical contact elements 54 and the lead insulators 36 engage the insulating rings 26. A first end portion 38 of the lead cable 32 is received within a recess 40 (FIG. 3A) defined in an end wall of the body portion 16 of the header 14. The first end portion 38 includes an annular groove 42 (FIG. 1) configured to receive a lead locking device 44, such as a set screw. The set screw 44 extends through a threaded opening 46 in the holding ring 22 (FIG. 4) and into the annular groove 42, as shown in FIG. 1. When tightened, the lead locking device 44 resists the withdrawal of the lead cable 32 from the header 14 in the axial direction. Although the holding ring 22 is shown as being located at the end wall of the header 14, it may be located anywhere along the header 14, including at the opposite end.

With reference to FIG. 1, the lead cable 32 further comprises a lead body 48, which carries a plurality of electrode leads 50. Ends (not shown) of the electrode leads 50 have electrode terminals (not shown) for providing electrical stimulation to body tissues at one or more locations remote from the IMD 10. The number of electrode leads 50 and the corresponding numbers of electrode terminals, electrical terminals 34 and contact rings 20 may vary depending on the particular application for which the IMD 10 is designed. Accordingly, applications of the IMDs 10 discussed herein include unipolar, bipolar, and multi-polar applications including varying numbers of components.

With reference to FIG. 2, FIG. 2A and FIG. 4, each of the contact rings 20 comprises an outer ring contact element 52 and a canted-coil spring contact element 54 housed in abutting engagement in the interior of the outer ring contact element 52. In the illustrated embodiment (FIG. 2A), each outer ring contact element 52 has a height (measured in the axial direction) that is substantially equal to the height of its respective canted-coil spring contact element 54. However, in alternative embodiments these components may have differing heights so that the outer ring contact element 52 biases the spring contact element 54. Further, in the illustrated embodiment the coils of the canted-coil spring contact element 54 are substantially circular. However, in alternative embodiments the coils could be shaped differently, such as oval, elliptical, square, and the like.

The outer ring contact element 52 and the canted-coil spring contact element 54 are each constructed of conductive materials and each outer ring contact element 52 is in electrical contact with its respective canted-coil spring contact element 54. With reference to FIG. 1, the ring contact elements 52 are each configured to pass an electrical signal from one of the electrical leads 24 to their corresponding outer ring contact element 52 and canted-coil spring contact element 54, which then passes the electrical signal to a corresponding electrical terminal 34 on the lead cable 32, and then onto a corresponding electrode lead 50 located inside the lead body 48, and then to a corresponding electrode terminal on the distal end of the lead cable 32.

The spring contact elements 54 may comprise canted-coil springs. In certain embodiments the springs may be radially canted, while in certain other embodiments the springs may be axially canted. In still further embodiments, the springs may be both radially canted and axially canted. Canted-coil springs are described in detail in U.S. Pat. Nos. 4,655,462; 4,826,144; 4,876,781; 4,907,788; 4,915,366; 4,964,204; 5,139,243; 5,160,122; 5,503,375; 5,615,870; 5,709,371; 5,791,638; and 7,055,812. The contents of each of the foregoing patents are hereby expressly incorporated by reference herein.

With reference to FIG. 4, in one embodiment the ring contact elements 52 are each generally cylindrical in configuration. Thus, each ring contact elements 52 has a generally constant inner diameter and outer diameter with two square ends, with normal manufacturing tolerance being acceptable. In this embodiment, the ring contact elements 52 do not have machined or formed grooves for forming contact grooves therein for accommodating the spring contact elements 54. The ring contact elements 52 have a simple profile, which in one embodiment is tubular in shape and makes manufacturing the contact rings 20 and assembling the spring contact elements 54 therein easier and therefore more cost effective. In other embodiments, the ring contact elements 52 inside diameter may include a groove in the area of the spring contact elements 54 so that two points of contact are available for the spring contact elements 54 versus one.

Other geometries are also contemplated. For example, the ring contact elements 52 may have a thicker section so that there are at least two internal diameters. The spring contact elements 54 can then be inserted through the larger internal diameter end of the ring contact elements 52 until it abuts the shoulder formed at the intersection between the two different internal diameters. Thus, different diameters and undulating internal surfaces for the ring contact elements 52 are contemplated. The ring with a grooved internal surface can be considered a sub-species of a ring having at least two internal diameters. Still alternatively, the plurality of ring contact elements 52 in a single connector assembly may be non-uniform. For example, one embodiment may include a grooved ring at a first end of the connector assembly and smooth rings for the remaining ring contact elements 52. Still alternatively, a ring with two different internal diameters may be combined with a grooved ring and with rings having uniform internal diameters. Thus, ring contact elements 52 provided herein can have not only a smooth internal diameter, but also machined surfaces and undulating surfaces.

With reference to FIGS. 1 and 2, the header 14 includes a protruding portion 56 at a first end. The protruding portion 56 is substantially cylindrical and coaxial with the openings 30 in the insulating rings 26 (FIG. 3A). As shown in FIG. 3B, an inner surface 58 of the protruding portion 56 includes anon-tapered region 60 adjacent an outward opening 62 in the protruding portion 56 and a tapered region 64 spaced from the outward opening 62. The tapered region 64 tapers outwardly with increasing distance from the outward opening 62. With reference to FIG. 2, the outward taper reduces the contact area between the protruding portion 56 and the lead cable 32, thus reducing frictional resistance to insertion and removal of the lead cable 32 with respect to the header 14. An inwardly projecting ring 66 (FIG. 3A) just inside the outward opening 62 forms an outermost insulating ring 26 that maintains a seal around the lead cable 32 to resist intrusion of bodily fluids into the IMD 10.

As recited above, in the present embodiments the header 14 may be formed as a unitary piece in which the insulating rings 26 are integrally formed with the header body 16. For example, the header 14 may be injection molded from a polymeric and/or elastomeric material, such as epoxy or silicone. The electrical contact rings 20 and the holding ring 22 are subsequently inserted through the openings 18 and into the spaced cavities 19 as shown in FIG. 4, and the cavities 19 and/or openings 18 may then be back-filled using a curable and implantable material. The header 14 is thus formed separately from the contact rings 20, and the two are subsequently combined. Once combined, the insulating rings 26 preferably engage the electrical contact rings 20 and the holding ring 22 in a snug fit or an interference fit on that there are no gaps between these components through which bodily fluids may penetrate to the lead cable 32.

Thus, in a method of assembling the header for an implantable medical device, a unitary body portion defining a plurality of openings spaced axially along a body portion and a plurality of elastomeric walls interdisposed between the adjacent openings defining cavities within the body portion is provided. Electrical contact rings each comprising an outer ring contact element and an electrical contact element housed in abutting engagement in an interior of the outer ring contact element are placed into each cavity. The insertion of the contact rings allows the capturing of electrical contact elements within the elastomeric walls of the cavities with no intervening portion of the electrical contact ring disposed between the electrical contact element and the elastomeric walls. By not incorporating ring contact sidewalls, the ring contact elements are shorter along an axial direction than comparable ring contact elements with ring contact sidewalls. Also by not incorporating ring contact sidewalls, the pitch or distance between two adjacent ring contact elements inside the header are shorter along the axial direction than comparable ring contact elements with ring contact sidewalls. This in turn allows for higher density or number of ring contact elements to be included in the header than ones having comparable ring contact elements with contact sidewalls. Furthermore, by having a higher density header, more electrode terminals may be incorporated with the medical lead cable for electrical stimulation of body tissues.

The header 14 engages an end of the can 12 as shown in FIG. 1. During assembly of the IMD 10, the header 14 may be secured to the can 12 prior to the contact rings 20 being inserted into the cavities 19, or vice versa. Preferably, however, the electrical leads 24 are placed as shown in FIGS. 1 and 3B after the header 14 is secured to the can 12 and the contact rings 20 are inserted into the cavities 19. This order of assembly steps prevents the electrical leads 24 from interfering with passage of the contact rings 20 into the cavities 19. The electrical leads 24 are placed such that each contacts a respective electrical contact ring 20.

The lead cable 32 is inserted into the header 14 as shown in FIGS. 1 and 2 such that the insulating rings 26 engage the lead insulators 36 and the turns of the spring contact elements 54 bear against the lead electrical terminals 34. With reference to FIG. 2A, the insulating rings 26 preferably engage the lead cable 32 in an interference fit to resist the penetration of bodily fluids into the interior of the header 14. In one embodiment, the interference fit may be about 0.001" or 0.002" radially. Similarly, the spring contact elements 54 are sized so that each is deflected by the lead cable 32. In one embodiment, the deflection is about 5% and up to about 50% of the spring contact elements' 54 total radial deflection, with up to about 40% being preferred. This deflection range ensures that a sufficient spring contact force is generated between the ring contact elements 52 and the electrical terminals 34 on the lead cable 32 for transferring electric signals between the two.

To secure the lead cable 32 within the header 14, the lead locking device 44 is advanced into the threaded bore 46 in the holding ring 22 until the lead locking device 44 extends into the groove 42 in the lead cable 32, as shown in FIG. 3B. Those of ordinary skill in the art will appreciate that in other embodiments the bore in the holding ring 22 may be smooth and the lead locking device may comprise a pin.

The interference fit described above creates friction on the lead cable 32 that resists axial insertion of the lead cable 32 into the header 14. With regard to the insulating rings 26, in conventional IMDs each insulating ring 26 primarily deflects by compression in the radially outward direction. This type of deflection creates a relatively high insertion force. As is clear to a person of ordinary skill in the art, the force is increased in a multi-seal in-line connector application due to insertion force across each seal.

With reference to FIGS. 3A and 3B, the present embodiments reduce the insertion force by providing insulating rings 26 having a relatively high slenderness ratio. As used herein the slenderness ratio is defined as the ratio of the insulating ring's length to its width, where length is measured in the radial direction and width is measured in the axial direction. The slenderness ratio is preferably greater than 1:1, and more preferably greater than 2:1, in order to achieve the desired low insertion force. Such slenderness ratios enable the insulating rings 26 to deflect a greater axial amount than conventional insulating rings. Such slenderness ratios further enable the insulating rings 26 to have decreased radial compression and increased axial deflection as compared to conventional insulating rings.

The present header 14 provides many advantages over prior art IMDs. For example, the header 14 is comparatively easy to manufacture and assemble. The header body 16 is molded as a unitary piece with the sealing rings 26. The contact rings 20 are then inserted through the openings 18 and into the cavities 19 and the cavities 19 are back filled to retain the contact rings 20 within the cavities 19. In back filling the cavities, the openings 18 are closed by the back filled material. The lead cable 32 is then inserted and secured with the lead locking device 44. In this process there are no complex steps of aligning contact rings 20 or sealing rings 26 and maintaining alignment while the lead cable 32 is inserted. The integral sealing rings 26 are already aligned, and the contact rings 20 are simply slid into place where friction keeps them in place until the lead cable 32 is inserted. The reduction in complexity of assembly also advantageously reduces the cost of manufacture for the present header 14.

A single connector assembly has thus far been described as being positioned inside the header 14; however, two or more connector assemblies may be positioned within the header if desired depending on the particular implant application. In some embodiments, the connector assemblies may be stacked side-by-side relative to the can 12. As shown in the embodiment of FIG. 5, an alternative header 14a may include connector assemblies stacked on top of one another relative to the can 12.

Figure 5:
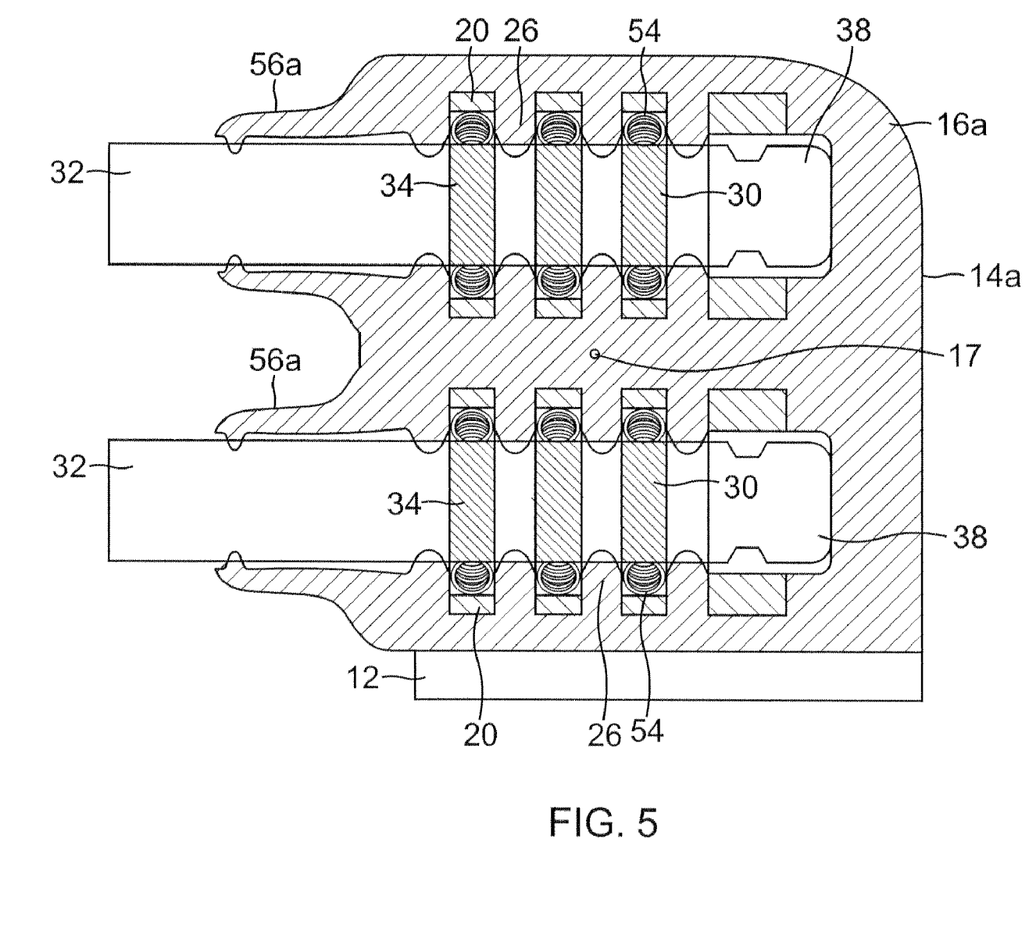
FIG. 5 is a cross-sectional view of an alternative IMD comprising a header having multiple connector assemblies.

In the alternative embodiment of FIG. 5, it should be understood that the connector assemblies formed in the alternative header 14a each comprise the same components, to provide the same functions and operate in the same manner as described above with regard to the single connector assembly disposed in header 14. As in previously described embodiments, each connector assembly includes the insulating rings 26 that separate the cavities 19 and electrically isolate each contact ring 20 from the neighboring contact rings 20. The insulating rings 26 also seal against the lead cable 32, as discussed above. Each insulating ring 26 substantially comprises the flat dividing wall 28 that defines the circular opening or aperture 30 at or near its center and axially aligned with the insulating ring 26. As described in detail above, in certain embodiments the insulating rings 26 are molded integrally with the header body. The header 14a with the contact rings 20, insulating rings 26 and holding ring 22 may comprise the plurality of connector assemblies stacked on to one another and configured to receive the medical lead cables 32.

Although the connector assemblies are the same as described above, the alternative header body portion 16a is reconfigured to accommodate the plurality of connector assemblies disposed therein. For example, in this embodiment, the body portion 16a is formed having a plurality of protruding portions 56a at a first end of the header 14a that correspond to each connector assembly disposed in the header 14a. Each protruding portion 56a is formed substantially cylindrical and positioned coaxial with the openings 30 in the insulating rings 26 of each connector assembly. The protruding portions 56a are similar in all additional respects to the protruding portion 56 described above.

In the body portion 16a of header 14a, an adequate space 17 of header body material is disposed between the connector assemblies to ensure adequate isolation between the stacked connector assemblies.

Header 14a includes and accommodates electrical leads 24 that extend between the power source in the can 12 and the contact rings 20 of each connector assembly. The leads 24 may project through one or more feed-through terminals (not shown) passing through the sealed can 12 and positioned on either side of the header body 16a to reach the contact rings 20. Since it is understood that the header 14a may be formed having any number of contact rings per connector assembly, it is also understood that the header 14a is formed to include the appropriate number of the leads 24 needed to accommodate the number of contact rings 20.

Although several embodiments of the present header 14 for IMDs have been specifically described and illustrated, many modifications and variations will be apparent to those skilled in the art. For example, various material changes may be incorporated, such as making use of two or more different materials or composites, different mechanical engagement means may be used to attach the various components to one another, etc. Accordingly, it is to be understood that the present embodiments may be embodied in other ways than as specifically described herein.

The above description presents the best mode contemplated for carrying out the present header for implantable medical devices, and of the manner and process of making and using it, in such full, clear, concise, and exact terms as to enable any person skilled in the art to which it pertains to make and use this header. This header is, however, susceptible to modifications and alternate constructions from that discussed above that are fully equivalent. Consequently, this header is not limited to the particular embodiments disclosed. On the contrary, this header covers all modifications and alternate constructions coming within the spirit and scope of the header as generally expressed by the following claims, which particularly point out and distinctly claim the subject matter of the header.

What is claimed is:

1. A header assembly for an implantable medical device (IMD) comprising:
  a body portion defining a plurality of openings spaced axially along the body portion;
  a plurality of elastomeric walls interdisposed between adjacent openings to define cavities within the body portion, each elastomeric wall defining an aperture passing axially therethrough; and
  a plurality of electrical contact rings each comprising an outer ring contact element and an electrical contact element housed in abutting engagement in an interior of the outer ring contact element, and configured to be positioned within the cavities such that adjacent elastomeric walls capture the electrical contact elements therebetween;
  wherein the elastomeric walls are formed unitarily with the body portion.

2. The header assembly of claim 1, wherein the body portion is configured to engage a sealed can of the IMD and to receive one or more lead cables.

3. The header assembly of claim 1, wherein the plurality of electrical contact rings are devoid of ring contact sidewalls.

4. The header assembly of claim 1, wherein the elastomeric walls comprise dielectric insulators.

5. The header assembly of claim 1, wherein the elastomeric walls comprise elastomeric seals for sealing against a lead cable.

6. The header assembly of claim 1, wherein the electrical contact element comprises a canted-coil spring.

7. The header assembly of claim 1, further comprising a protruding portion at a first end of the body portion, the protruding portion being substantially cylindrical and coaxial with the apertures.

8. The header assembly of claim 7, wherein the protruding portion comprises an inner surface including a non-tapered region adjacent an outward opening in the protruding portion and a tapered region spaced from the outward opening.

9. The header assembly of claim 8, further comprising an inwardly projecting ring located immediately inside the outward opening.

10. The header assembly of claim 1, wherein the body portion defines a plurality of second openings spaced axially along the body portion;
  a plurality of elastomeric walls interdisposed between the adjacent second openings to define second cavities within the body portion, each elastomeric wall defining an aperture passing axially therethrough; and
  a plurality of second electrical contact rings each comprising an outer ring contact element and an electrical contact element housed in abutting engagement in an interior of the outer ring contact element, and configured to be positioned within the second cavities such that the elastomeric walls capture the electrical contact elements therebetween.

11. A header assembly for an implantable medical device (IMD) comprising:
  a body portion defining a plurality of first openings spaced axially along the body portion;
  a plurality of elastomeric walls interdisposed between the adjacent first openings to define first cavities within the body portion, each elastomeric wall defining an aperture passing axially therethrough; and
  a first plurality of electrical contact rings positioned within the cavities between the elastomeric walls to form channels wherein the elastomeric walls form side walls of the channel and the electrical contact ring forms a base wall of the channel, the side walls configured to capture a canted-coil spring housed within the electrical contact rings with no intervening portion of the electrical contact ring disposed between the canted-coil spring and the side walls;
  wherein the elastomeric walls are formed unitarily with the body portion.

12. The header assembly of claim 11, wherein the body portion is configured to engage a sealed can of the IMD and to receive one or more lead cables.

13. The header assembly of claim 11, wherein the elastomeric walls comprise dielectric insulators and elastomeric seals between the electrical contact rings.

14. The header assembly of claim 11, further comprising:
  a protruding portion at a first end of the body portion, the protruding portion substantially cylindrical and coaxial with the apertures, wherein the protruding portion comprises an inner surface including a non-tapered region adjacent an outward opening in the protruding portion and a tapered region spaced from the outward opening, and an inwardly projecting ring immediately inside the outward opening that maintains a seal around a cable inserted into the outward opening.

15. The header assembly of claim 11, wherein the body portion defines a plurality of second openings spaced axially along the body portion; a plurality of elastomeric walls interdisposed between the adjacent second openings to define second cavities within the body portion, each elastomeric wall defining an aperture passing axially therethrough; and a second plurality of electrical contact rings positioned within the second cavities between the elastomeric walls to form channels wherein the elastomeric walls form side walls of the channel and the electrical contact ring forms a base wall of the channel, the side walls configured to capture the canted-coil springs housed within the electrical contact rings.

16. A method of assembling a header for an implantable medical device (IMD) comprising:
providing a unitary body portion defining a plurality of openings spaced axially along the body portion, and a plurality of elastomeric walls interdisposed between the adjacent openings to define cavities within the body portion, each elastomeric wall defining an aperture passing axially therethrough;

inserting an electrical contact ring comprising an outer ring contact element and an electrical contact element housed in abutting engagement in an interior of the outer ring contact element into each cavity; and capturing the electrical contact elements within the elastomeric walls of the cavities with no intervening portion of the electrical contact ring disposed between the electrical contact element and the elastomeric walls.

17. The method of claim 16 wherein the unitary body further comprises:
a protruding portion at a first end of the unitary body portion, the protruding portion substantially cylindrical and coaxial with the apertures, wherein the protruding portion comprises an inner surface including a non-tapered region adjacent an outward opening in the protruding portion and a tapered region spaced from the outward opening, and an inwardly projecting ring immediately inside the outward opening that maintains a seal around a cable inserted into the outward opening.

18. The method of claim 16, further comprising:
engaging the unitary body portion with a sealed can of an IMD; and
receiving one or more lead cables of the IMD for transmitting electrical pulses from the IMD to a location in a patient's body remote from the IMD.

* * * * *